(12) United States Patent
Goetz et al.

(10) Patent No.: US 8,164,747 B2
(45) Date of Patent: Apr. 24, 2012

(54) APPARATUS, SYSTEM AND METHOD FOR OPTICAL SPECTROSCOPIC MEASUREMENTS

(75) Inventors: Alexander F. H. Goetz, Boulder, CO (US); Leonid G. Feldman, Broomfield, CO (US); Thomas Ciupak, Longmont, CO (US); Robert J. Faus, Longmont, CO (US); Brian Curtiss, Boulder, CO (US)

(73) Assignee: ASD, Inc, Boulder, CO (US)

( * ) Notice: Subject to any disclaimer, the term of this patent is extended or adjusted under 35 U.S.C. 154(b) by 843 days.

(21) Appl. No.: 11/956,245

(22) Filed: Dec. 13, 2007

(65) Prior Publication Data

US 2008/0144012 A1    Jun. 19, 2008

Related U.S. Application Data

(60) Provisional application No. 60/870,053, filed on Dec. 14, 2006.

(51) Int. Cl.
*G01J 3/00* (2006.01)

(52) U.S. Cl. ........................................... 356/300

(58) Field of Classification Search ............... 356/72–73, 356/300
See application file for complete search history.

(56) References Cited

U.S. PATENT DOCUMENTS

| | | | |
|---|---|---|---|
| 5,842,995 A | 12/1998 | Mahadevan-Jansen | |
| 6,067,156 A | 5/2000 | Slater | |
| 6,711,426 B2 | 3/2004 | Benaron | |
| 2005/0254049 A1* | 11/2005 | Zhao et al. | 356/369 |
| 2006/0192957 A1* | 8/2006 | Frick et al. | 356/328 |
| 2007/0132993 A1* | 6/2007 | Shibata | 356/328 |

FOREIGN PATENT DOCUMENTS

WO   PCT/US2007/87570     12/2007

* cited by examiner

*Primary Examiner* — Tarifur Chowdhury
*Assistant Examiner* — Abdullahi Nur
(74) *Attorney, Agent, or Firm* — Cooley LLP

(57) ABSTRACT

A system and method for optical spectroscopic measurements is described. One embodiment includes a measurement head for optical spectroscopic measurements, the measurement head comprising an illumination source configured to illuminate a sample, a collection optic configured to view the sample, and an internal reference, wherein the internal reference can be illuminated by the illumination source and viewed by the collection optic.

23 Claims, 15 Drawing Sheets

APPARATUS, SYSTEM AND METHOD FOR OPTICAL SPECTROSCOPIC MEASUREMENTS

PRIORITY

The present application claims priority to commonly owned and assigned application No. 60/870,053, filed Dec. 14, 2006, entitled Apparatus, System and Method for Optical Spectroscopic Measurements, which is incorporated herein by reference.

FIELD OF THE INVENTION

The present invention relates to apparatus, systems and methods for optical spectroscopic measurements. In particular, but not by way of limitation, the present invention relates to systems and methods for optical spectroscopic measurements of solids in manufacturing, industrial, or other in-process or at-line settings.

BACKGROUND OF THE INVENTION

Many manufacturing processes benefit from in-process measurement of product composition or quality. Optical spectroscopy is one means to perform these measurements. For non-turbid liquids, transmission spectroscopy is a commonly used method. For many other materials, non-contact forms of optical spectroscopy (e.g. reflectance, fluoresce, Raman) are often suited to these applications.

Unlike laboratory measurements that are performed under controlled conditions, in-process or at-line measurements typically must contend with the existing conditions in the manufacturing environment. In general, the accuracy of compositional or quality information derived from a spectroscopic measurement is related to the accuracy with which the optical spectrum was measured. This in turn is influenced, in large part, by the design of the measurement head that illuminates the sample, collects the illumination reflected back or emitted by the sample under inspection, and then delivers that collected illumination to the instrument performing the optical spectrum measurement.

Many parameters relating to a measurement head influence the accuracy. For example, such parameters include the frequency of the reference measurement, the instrument and illumination source status, the sample geometry, the sample surface texture, the ambient illumination, the secondary illumination and any stray (or scattered) illumination. Each of these parameters is described more completely below.

Frequency of the reference measurement: The optical spectrum of a sample is typically computed as a ratio of the spectroscopic instrument's response to the sample divided by the instrument's response to a reference sample. Since both the instrument's response function and the illumination or excitation source change or drift over time, the longer the time interval between measuring the reference and measuring the sample, the larger the error in the measured optical spectrum.

Instrument and illumination source status: The ability to monitor the condition of the spectroscopic instrument, illumination source and other aspects of the measurement system is critical to the long-term function of the system in this application.

Sample geometry: The physical location and orientation of the sample relative to the measurement head influence the observed optical spectrum since the characteristics of the measurement head's illumination (intensity and spectral distribution) vary positionally. Thus, the degree to which the illumination characteristics vary spatially and the variability of the sample's position relative to the measurement head combine to influence the accuracy of the measured optical spectrum.

Sample surface texture: The sample's surface texture and the illumination-to-collection angle determine the amount of shadowing 'seen' by the measurement head. Thus, larger illumination-to-collection angle combined with variation in sample texture results in greater variation of the observed optical spectrum.

Ambient illumination: In order to acquire an accurate optical spectrum, the ratio of the illumination characteristics (intensity and spectral distribution) when measuring the sample to that when measuring the reference must be known. Any time-varying illumination from sources other than the measurement head will lead to errors in the measured optical spectrum.

Secondary illumination: Illumination that strikes the sample, reflects back onto a secondary surface (e.g. some part of the measurement head or any other surface in the vicinity of the measured sample), and then re-illuminated the sample results in errors in the measured optical spectrum.

Stray (or scattered) illumination: Illumination that scatters off of any surface (other than the sample) that is viewed by the illumination collecting optics (e.g. an optical window. This results in an offset error in the measured optical spectrum.

Industrial applications requiring the measurement of an optical spectrum typically have some means to perform a reference measurement. In some cases this is performed manually: a reference sample is introduced into the field-of-view of the sampling head and measured. Subsequent sample measurements are divided by the reference in order to compute the desired optical spectrum. Another approach is available when fiber optics are used to deliver collected illumination: a fiber optic multiplexer provides the means to alternately view the illumination collected from the reference and sample(s). Such a multiplexer has multiple ports used for collected illumination inputs (e.g. reference plus one or more sample inputs) plus the means to direct the illumination from one of these inputs to a single output port. The illumination received at the output port is then delivered to the spectroscopic instrument.

Although present devices are functional, they are not sufficiently accurate or otherwise satisfactory. Accordingly, a system and method are needed to address the shortfalls of present technology and to provide other new and innovative features.

SUMMARY OF THE INVENTION

Exemplary embodiments of the present invention that are shown in the drawings are summarized below. These and other embodiments are more fully described in the Detailed Description section. It is to be understood, however, that there is no intention to limit the invention to the forms described in this Summary of the Invention or in the Detailed Description. One skilled in the art can recognize that there are numerous modifications, equivalents and alternative constructions that fall within the spirit and scope of the invention as expressed in the claims.

The present invention can provide a system and method for optical spectroscopic measurements. In one exemplary embodiment, the present invention can include a measurement head for optical spectroscopic measurements, the measurement head comprising an illumination source configured to illuminate a sample, a collection optic configured to view the sample, and an internal reference, wherein the internal reference can be illuminated by the illumination source and viewed by the collection optic.

As previously stated, the above-described embodiments and implementations are for illustration purposes only. Numerous other embodiments, implementations, and details of the invention are easily recognized by those of skill in the art from the following descriptions and claims.

BRIEF DESCRIPTION OF THE DRAWINGS

Various objects and advantages and a more complete understanding of the present invention are apparent and more readily appreciated by reference to the following Detailed Description and to the appended claims when taken in conjunction with the accompanying Drawings wherein:

DETAILED DESCRIPTION

Figure 1:
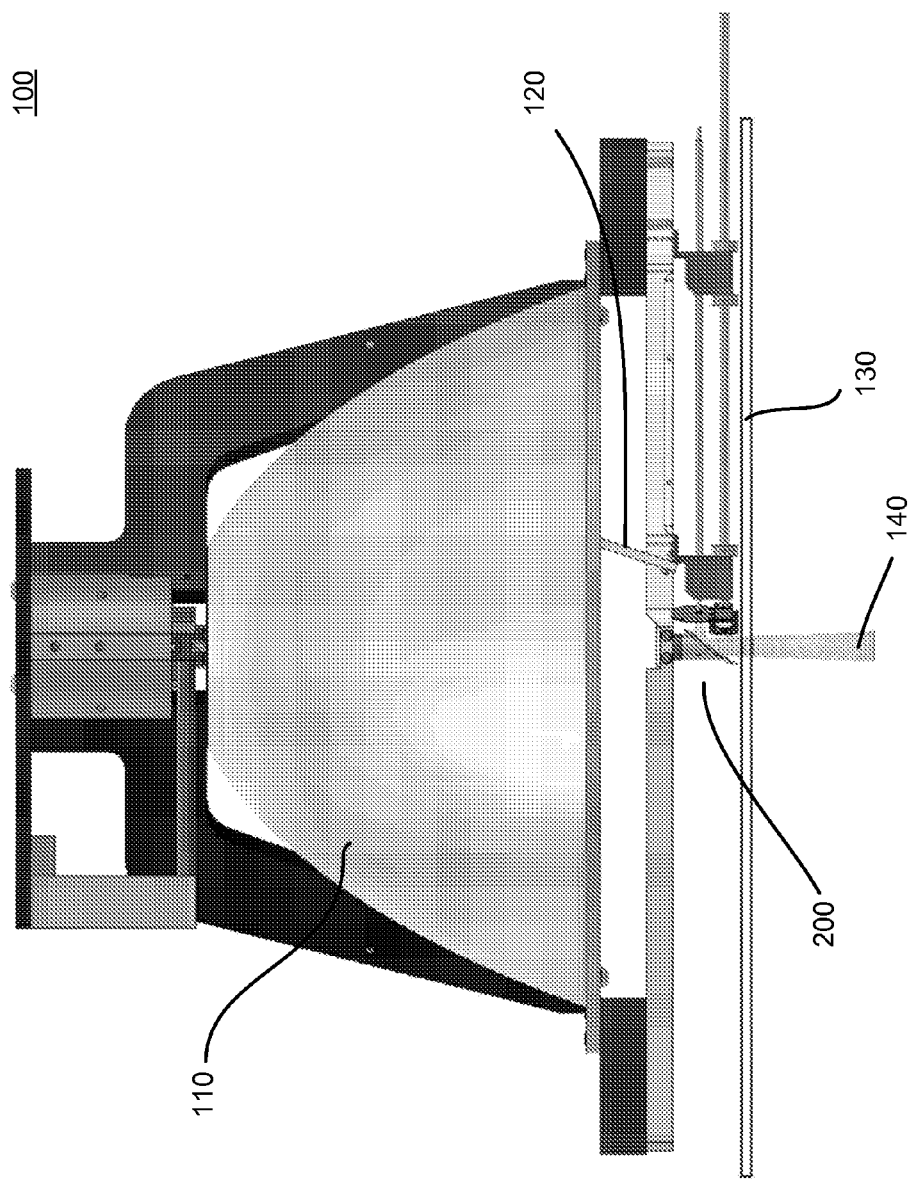
FIG. 1 is an illustration of a measurement head in accordance with one embodiment of the present invention.

Referring now to the drawings, where like or similar elements are designated with identical reference numerals throughout the several views, and referring in particular to FIG. 1, it illustrates a measurement head 100 constructed in accordance with one embodiment of the present invention. The measurement head 100 shown in FIG. 1 is designed to install over a conveyor belt carrying a time-varying material load that results in a variation in sample height (e.g., +/−0.5 meter variation).

In the embodiment shown in FIG. 1, an illuminator reflector 110 partially surrounds an illumination source 310. Between the illuminator reflector 110 and a sample (not shown) are optical elements 200 for the collection of reflected signals from a sample and an internal reference 120. Also shown in FIG. 1 is a window 130 which protects and shields the measurement head from process conditions. In one embodiment, the window 130 is a crown glass window.

This design simultaneously addresses two issues that are mutually exclusive in existing designs: while an on-axis design minimizes errors associated with sample surface texture, it results in increased errors associated with illumination spatial variability since the on-axis collection optics obscure a portion of the illumination beam. In this embodiment, the illuminator reflector 110 has a large diameter and long focal length which makes it possible to place the optical elements 200 in the near-field of the illuminator reflector 110 without significantly reducing the light output at the focus, or sample plane (not shown), by obscuration. This allows the measurement head to collect an optical ray bundle 140 from the sample that is on-axis with the illumination beam originating from the illumination source 310 and directed to the sample by the illuminator reflector 110 while minimizing errors due to obscuration of the sample. The on-axis design, as well as the long focal length, minimize the impacts of varying sample position and sample texture. Those skilled in the art will be aware of modifications and variations consistent with the present invention.

Figure 2:
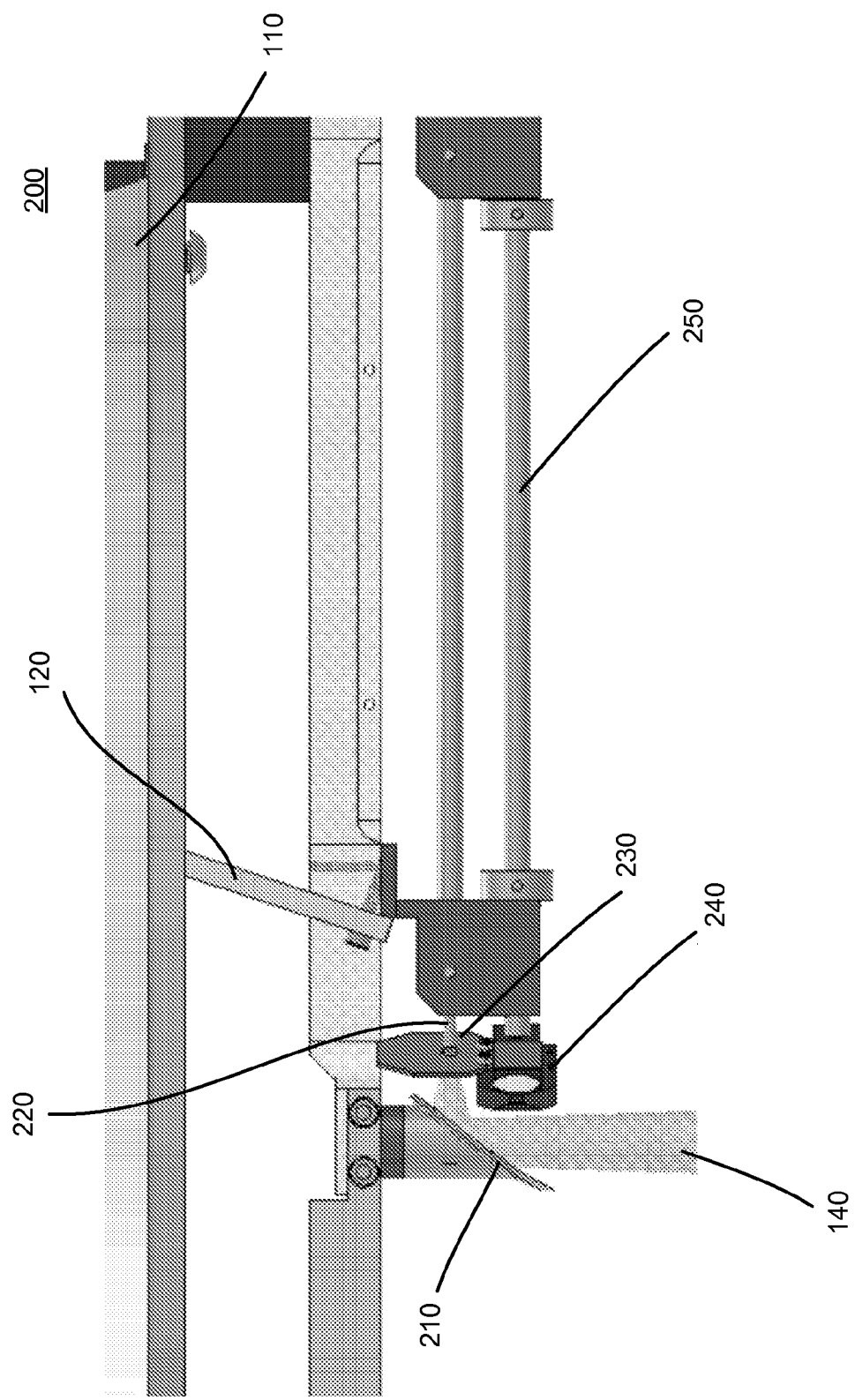
FIG. 2 is an enlarged illustration of the optical elements shown in FIG. 1 in the measurement position.

Referring to FIG. 2, it is a further illustration of the optical elements 200 from FIG. 1. Here, the optical elements 200 are shown in the measurement position, collecting incoming light from a sample 140. In the measurement position, the incoming light 140 is turned and focused by an off-axis parabolic mirror (OAP) 210 such that the light enters the fiber bundle collection optic 220 through a hole in the diffuser radiation shield 230. This shield 230 helps keep stray light from illuminating the OAP 210 and potentially reaching the collection optics 220. Those skilled in the art will be aware of many variations and modifications to the geometry of the optical window, as well as other components of the measurement head 100, in order to minimize secondary and stray illumination. Those skilled in the art will also be aware of many variations and modifications to the optical characteristics of the OAP 210, as well as other components of the measurement head 100, in order to optimize the system for the measurement head to sample distance and the size of the measured area. In another embodiment, the measurement head 100 could employ a high intensity illumination source 310 that minimizes the effect of ambient illumination. For example, the irradiance produced by the illumination source 310 using a 575 W bulb in one exemplary embodiment is 2.6 Wm-2 nm-1 at 2200 nm, approximately 20 times the solar irradiance. In yet another embodiment, scattered light from the enclosure window is reduced (e.g., to less than 0.5% of the signal from a 100% reflective surface) by shading the portion of the window directly below the OAP 210. Other variations and solutions consistent with the present invention will be obvious to those skilled in the art.

Figure 3:
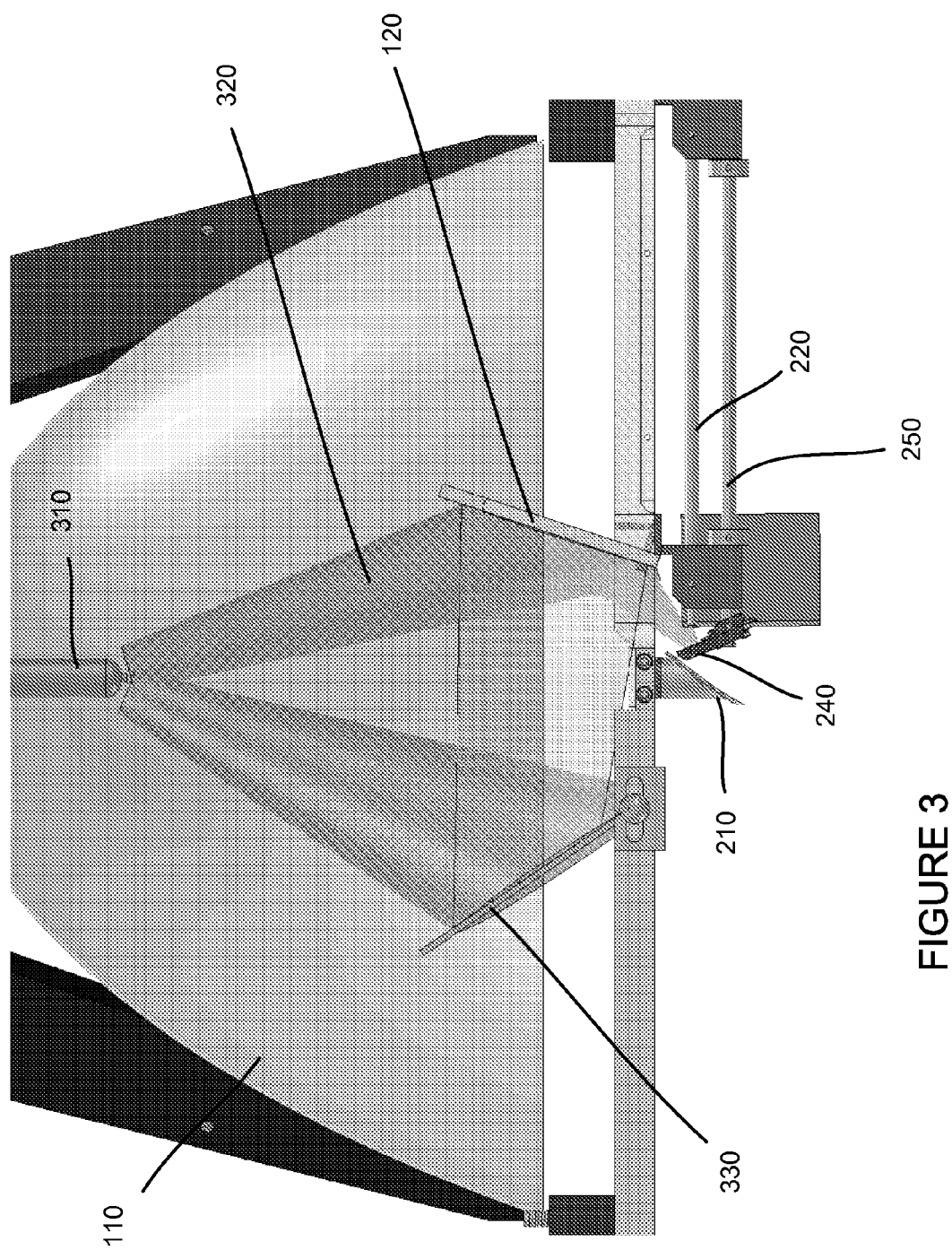
FIG. 3 is an illustration of a measurement head in a calibration position in accordance with one embodiment of the present invention.

Also shown in FIG. 2 is a calibration mirror 240, for viewing an internal reference 120, and a mirror rotation shaft 250. Also mounted to the same mirror rotation shaft 250 is the diffuser radiation shield 230. In accordance with one embodiment of the present invention, an internal reference measurement may be used to provide for the frequent measurement of a reference signal. In the measurement position, the diffuser radiation shield 230 shields the collecting optics 220 from stray illumination and the calibration mirror 240 is turned so as to not obscure the incoming light 140 from the collection optics 220. In order to take a calibration measurement, the mirror rotation shaft 250 can be rotated until the diffuser radiation shield 230 is rotated out of the incoming light beam 140 and the calibration mirror 240 blocks the collection optic 220 from viewing the sample and allows the collection optic to view the internal reference 120. This is shown in FIG. 3. Those skilled in the art will be aware of many modifications and variations, consistent with the present invention, for allowing the same collection optic to view a sample and an internal reference.

Figure 4:
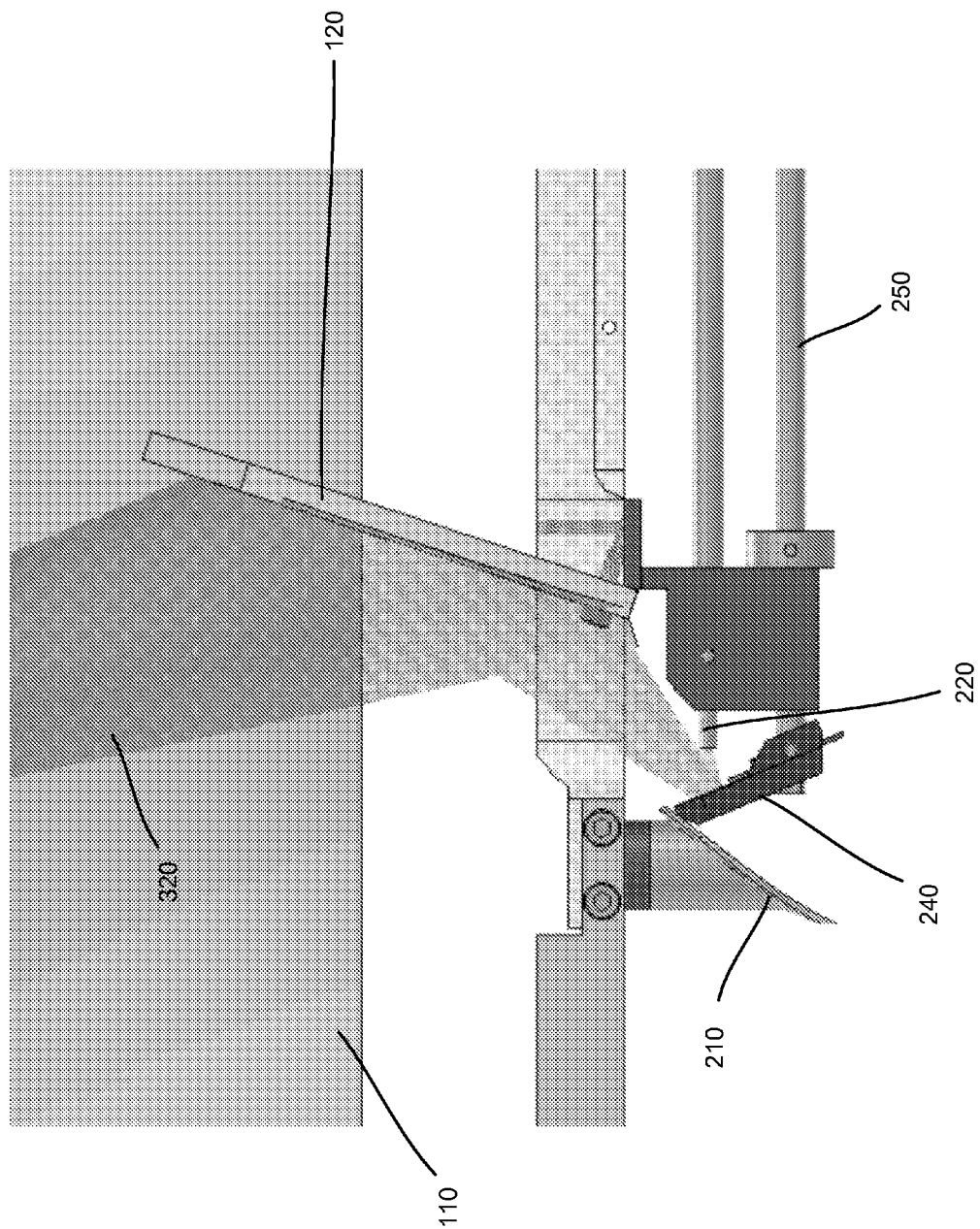
FIG. 4 is an enlarged illustration of the optical elements shown in FIG. 3.

As shown in FIG. 3, light 320 from the illumination source 310 is reflected off the internal reference 120 and redirected by the calibration mirror 240 into the collection optic 220. The shape, size and orientation of the internal reference 120 can be selected in order to more closely match the illumination level provided by the internal reference 120 to that seen by the system when viewing the sample, and in order to minimize any problems with obscuration. In accordance with one embodiment of the present invention, a reference mirror 330 which adds additional light to the internal reference 120 may be employed in order to more closely approach the signal intensity that would be received from an external reflectance standard. FIG. 4 shows may of these same components (again, in the internal reference viewing mode) in more detail.

In another embodiment of the present invention, a polycarbonate UV shield (not shown) could be rotated to cover the internal reference 120 while the measurement head is in the measurement position. The UV shield could be used to protect the standard 120 from aging which produces reflectance changes, particularly in the visible region of the spectrum.

Figure 5:
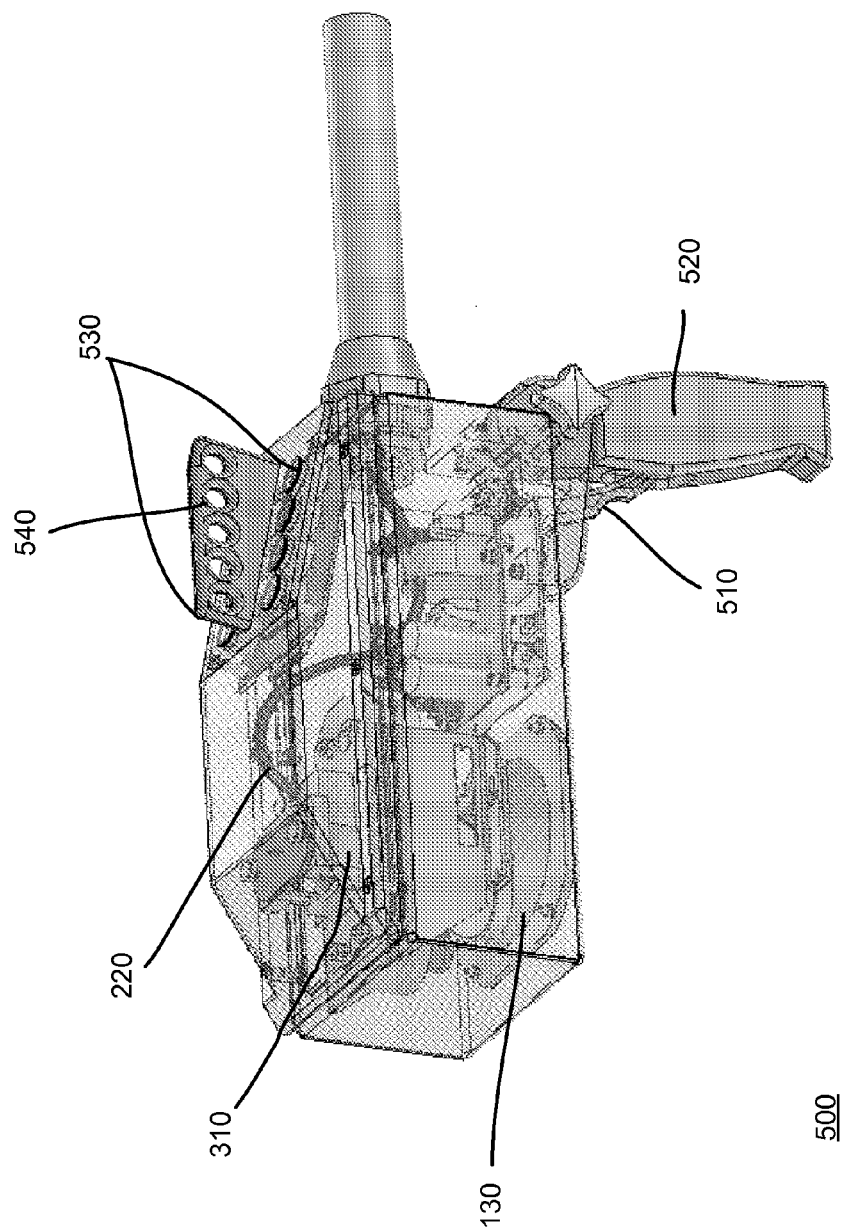
FIG. 5 is an illustration of a self-contained measurement head device in accordance with one embodiment of the present invention.

Now referring to FIG. 5, illustrated there is a self-contained measurement head device 500 designed in accordance with the present invention to measure reflectance optical spectra of flat surfaces. While the exemplary embodiment shown here was designed specifically for the measurement of beef carcasses, it is certainly not limited thereto and the design is easily adapted to other applications requiring reflectance measurements.

In this embodiment, the device 500 is configured for ease of use by an operator. Accordingly, the measurement head in FIG. 5 shows a device 500 with: a trigger 510 built into the grip 520 where the trigger 510 allows the operator to easily command the system to collect a sample measurement; an adjustable grip 520; a series of status lights 530 to inform the operator of various conditions—"measuring," "remeasure," "measurement complete," etc.; two rows of status lights 530 to allow the status to be determined from both sides of the device 500; and a tool hanger plate 540 that allows the device 500 to be suspended from a tool hanger (supports the weight of the device 500).

Figure 6:
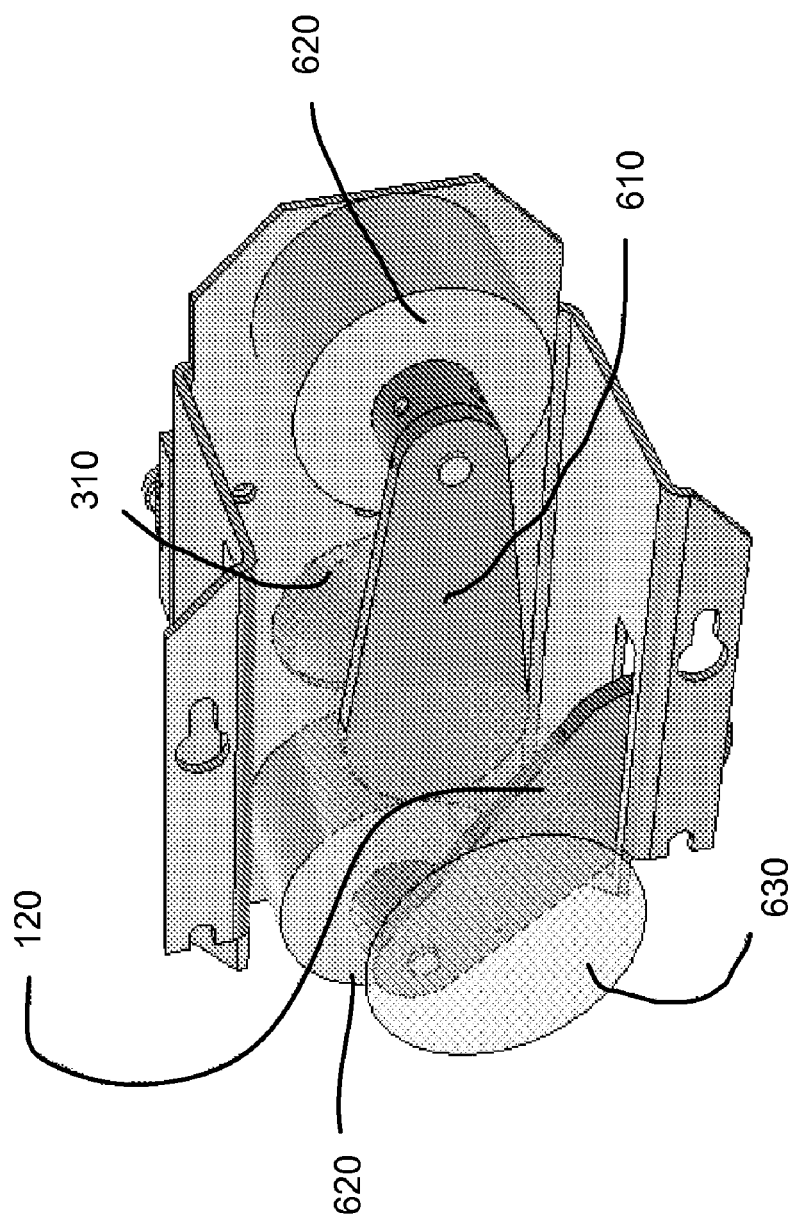
FIG. 6 is an illustration of a reference shutter arrangement in accordance with one embodiment of the present invention.

As above, the device 500 demonstrates an approach to perform reference measurements and monitor instrument system status without the requirement for operator intervention. Referring now to FIG. 6, the device 500 does this by incorporating an illumination source 310 and two references 120, 610 into the measurement head 500. In FIG. 6, the internal references are incorporated into shutters 120, 610 and require no operator intervention to perform periodic reference measurements. In FIG. 6, the first reference 120 is the standard reference used to compute the reflectance of the sample. The second reference 610 is composed of a material with absorption features at known wavelength and is used to verify the wavelength calibration of the instrument. Each shutter reference 120, 610 may be rotated into the illumination beam 630 using an actuator 620 such that the illuminated reference is viewed by the collection optic 220 that then delivers the collected reference illumination to the spectroscopic instrument (not shown). The reference measurement can also be used to monitor the condition of the illumination source 310 (bulb age, color temperature, stability, etc.).

These internal reference measurements have been shown to be much more reproducible than a manually positioned external reference. Moreover, the use of a second wavelength reference allows for the monitoring of spectrometer wavelength calibration.

Figure 7:
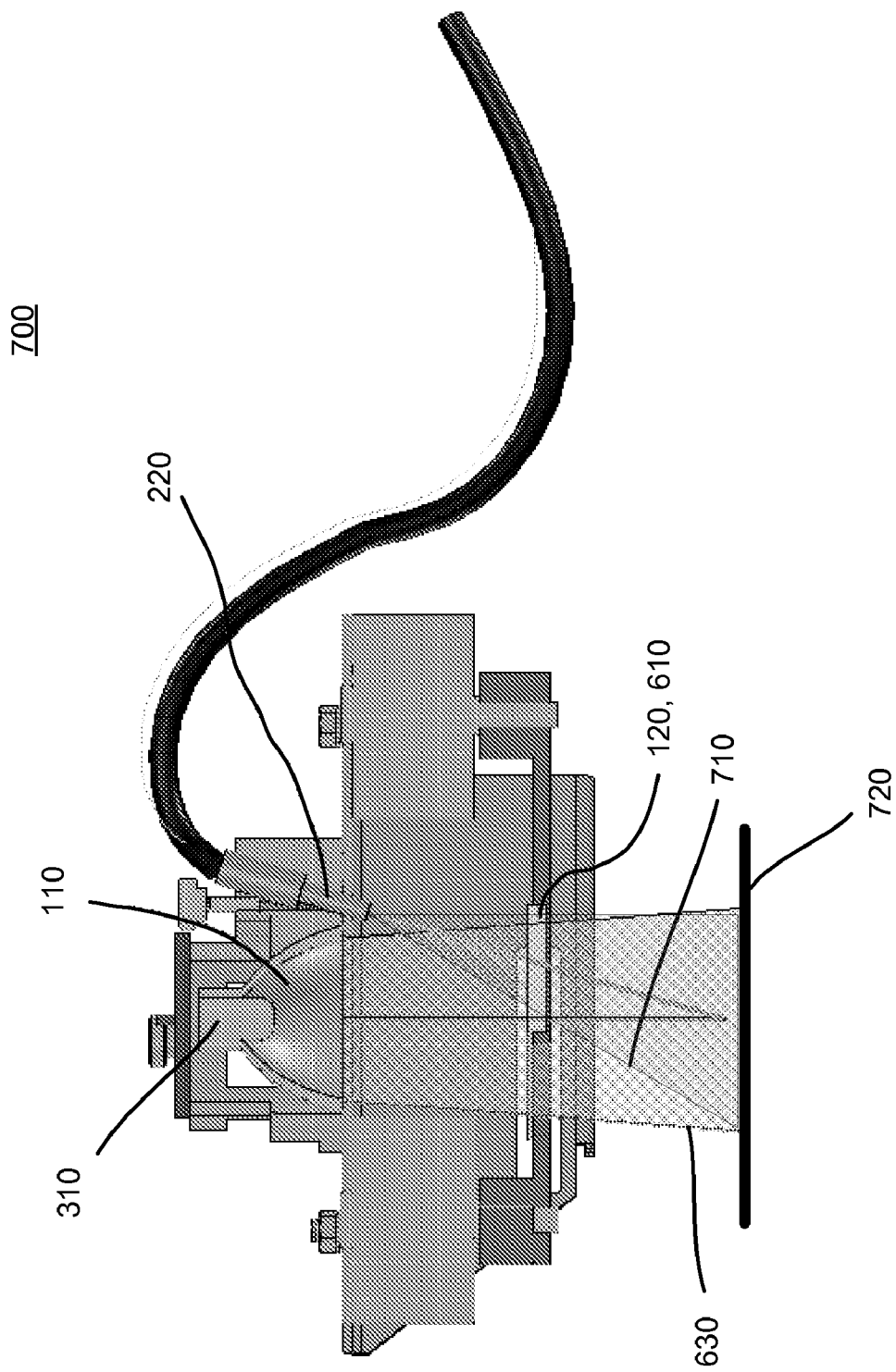
FIG. 7 is an illustration of a measurement head in accordance with one embodiment of the present invention.

As shown in FIG. 7, both the illumination source 310 and collection optic 220 are positioned such that the angular field-of-view 710 of the collection optic 220 views the area illuminated by the illumination beam 630 generated by the illumination source 310. The area viewed is at the intersection of the collection optics 220 angular field-of-view 710 and the illumination beam 630, and is coincident with the lower planar surface 720 of the device 500. It is this lower surface 720 which is placed in contact with the sample to assure a repeatable measurement.

In this embodiment, there is also an optical window 130 that isolates the interior of the measurement head 100 from the sample. This window 130 is recessed from the sample plane 720 in order to maintain the cleanliness of the window 130. The position and orientation of the window 130 is selected to preclude any specular (mirror) reflected illumination from reaching, or being delivered to, the collection optic 220.

Those skilled in the art will be aware of many modifications and variations to measurement heads and spectroscopic measurement systems in accordance with the present invention.

Figure 8:
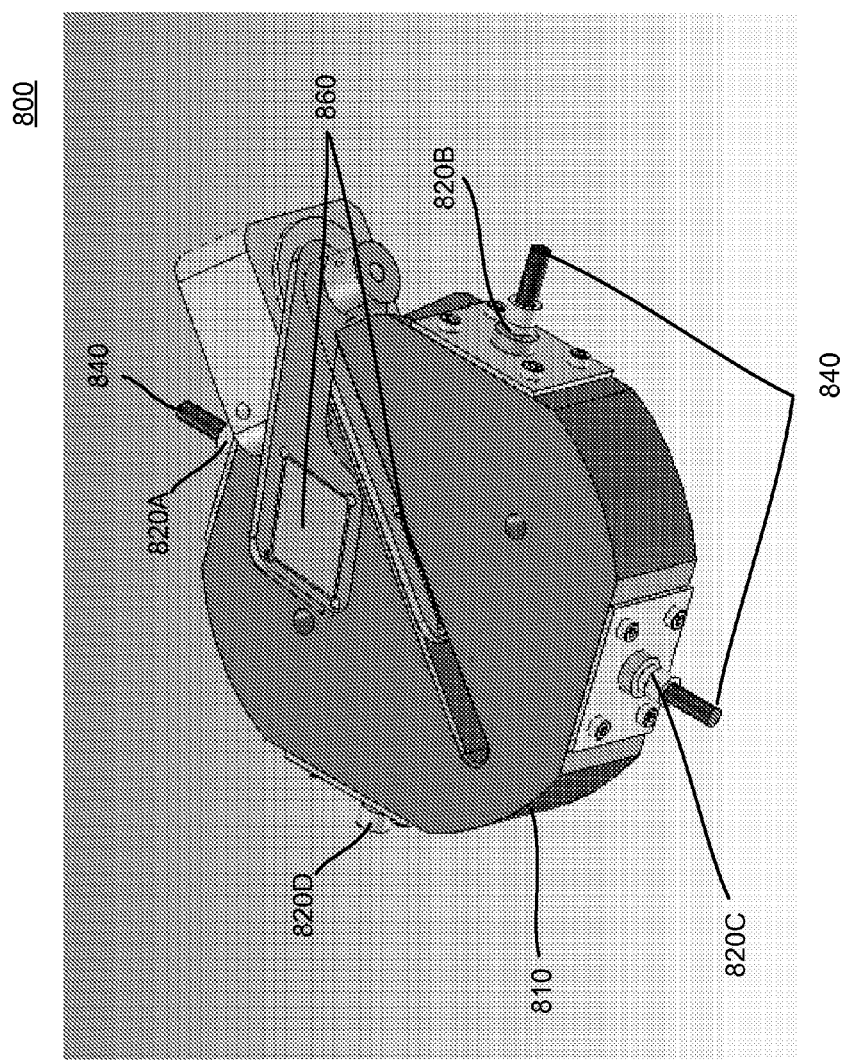
FIG. 8 is an illustration of an external view a device for alternating measurements in a spectroscopic measurement system in accordance with one embodiment of the present invention, where a paddle is shown in both the inserted and withdrawn positions.
Figure 9:
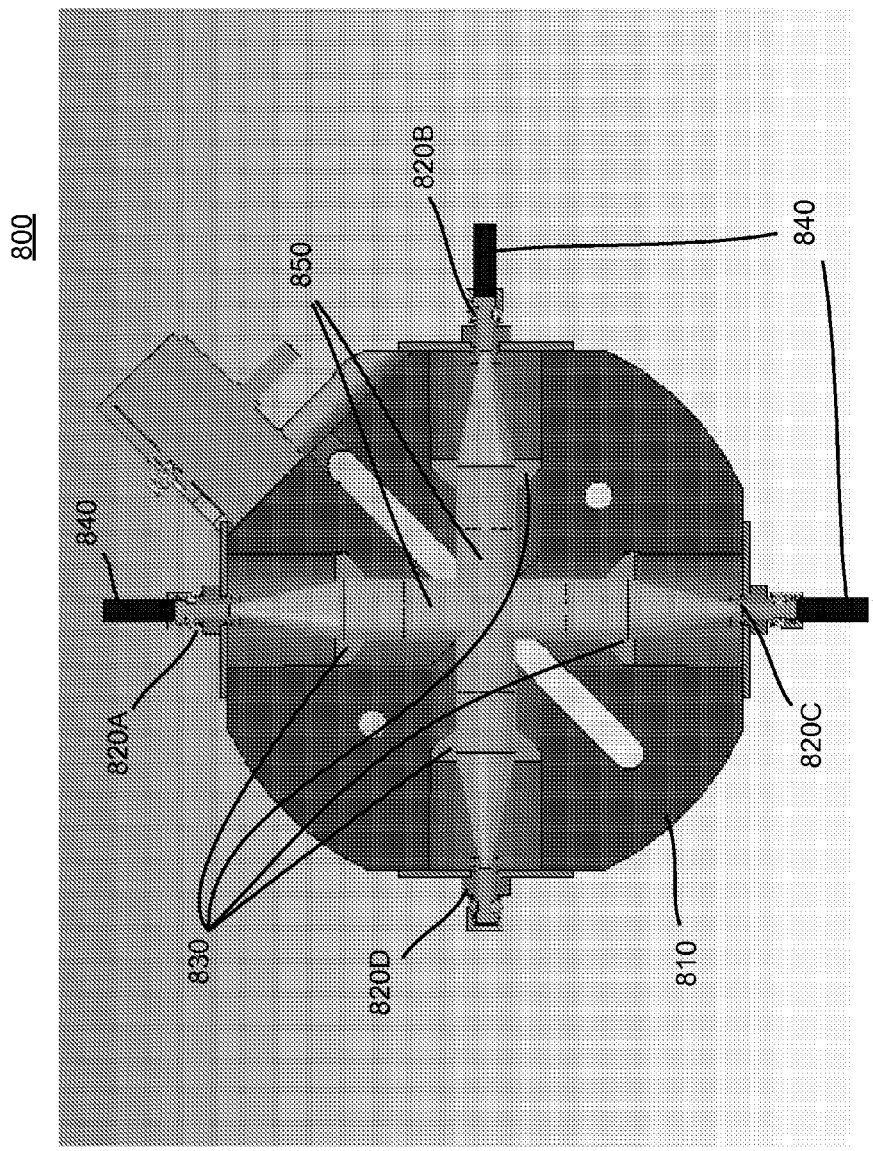
FIG. 9 is an illustration of a cut-away view a device for alternating measurements in a spectroscopic measurement system in accordance with one embodiment of the present invention, where the paddle is in the withdrawn position.
Figure 10:
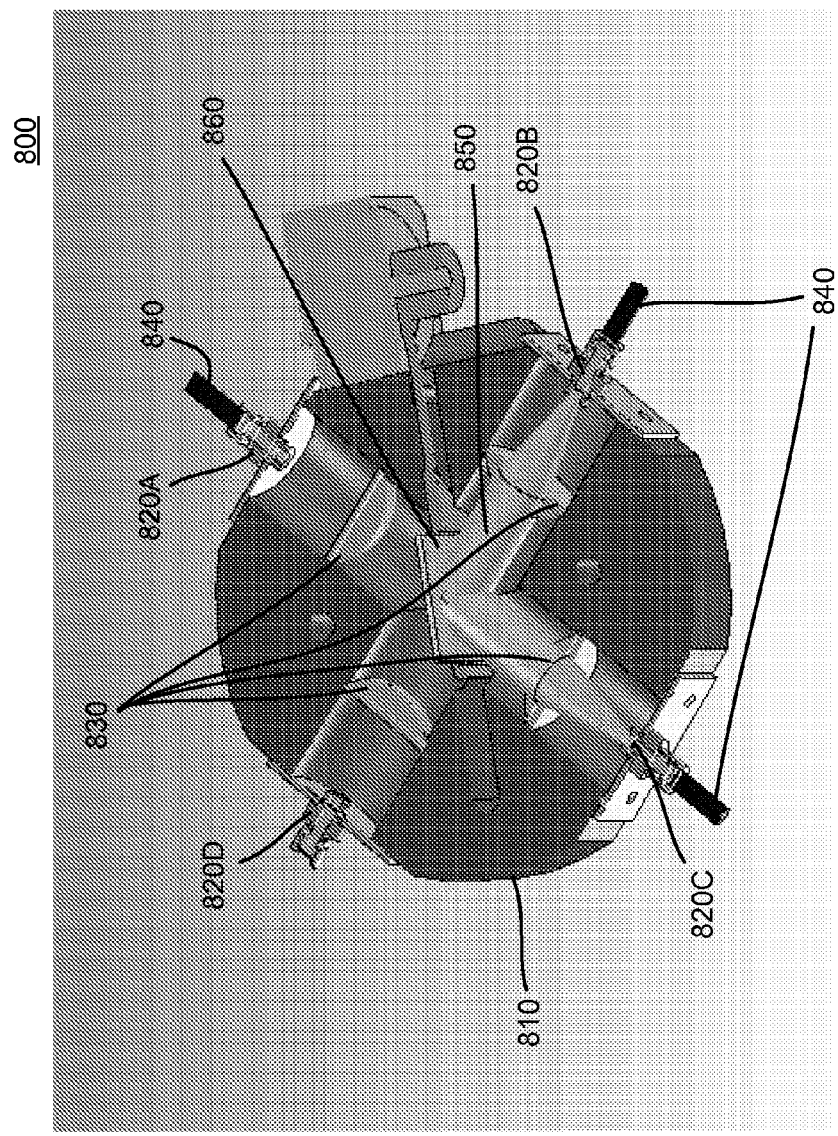
FIGS. 10-11 are illustrations of a cut-away view a device for alternating measurements in a spectroscopic measurement system in accordance with one embodiment of the present invention, where a paddle is shown in the inserted position.
Figure 11:
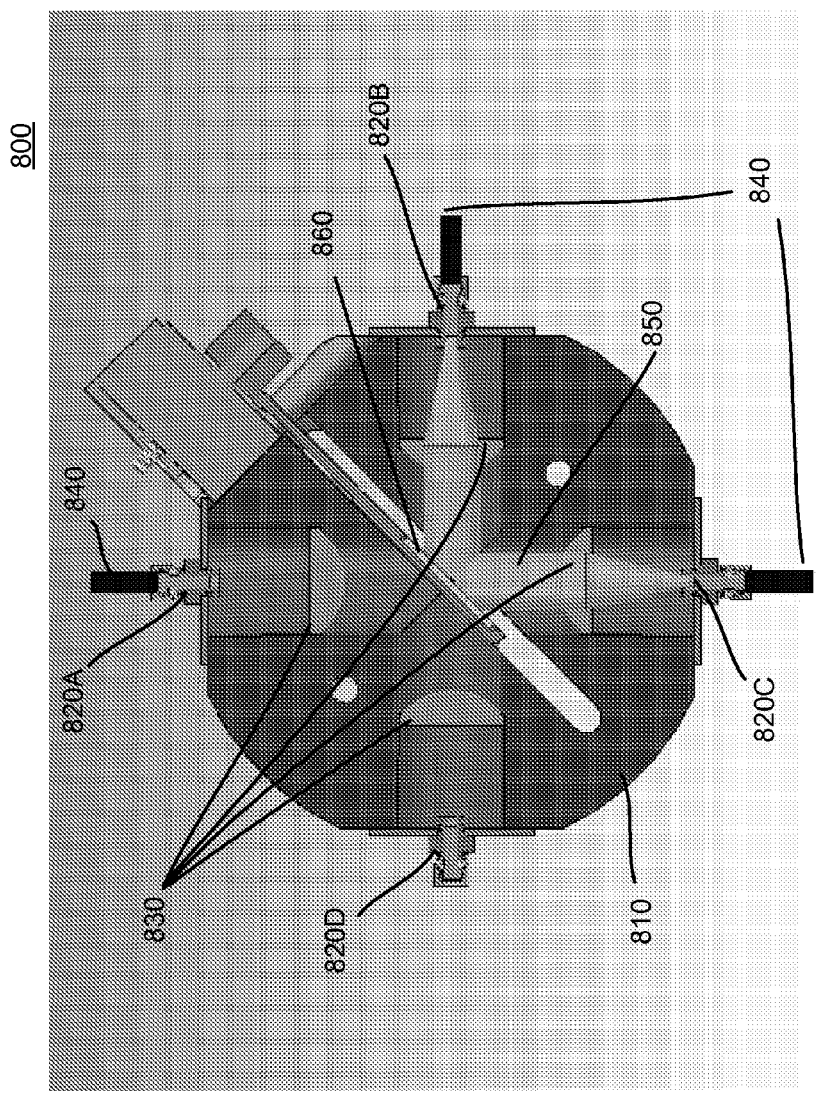
Figure 12:
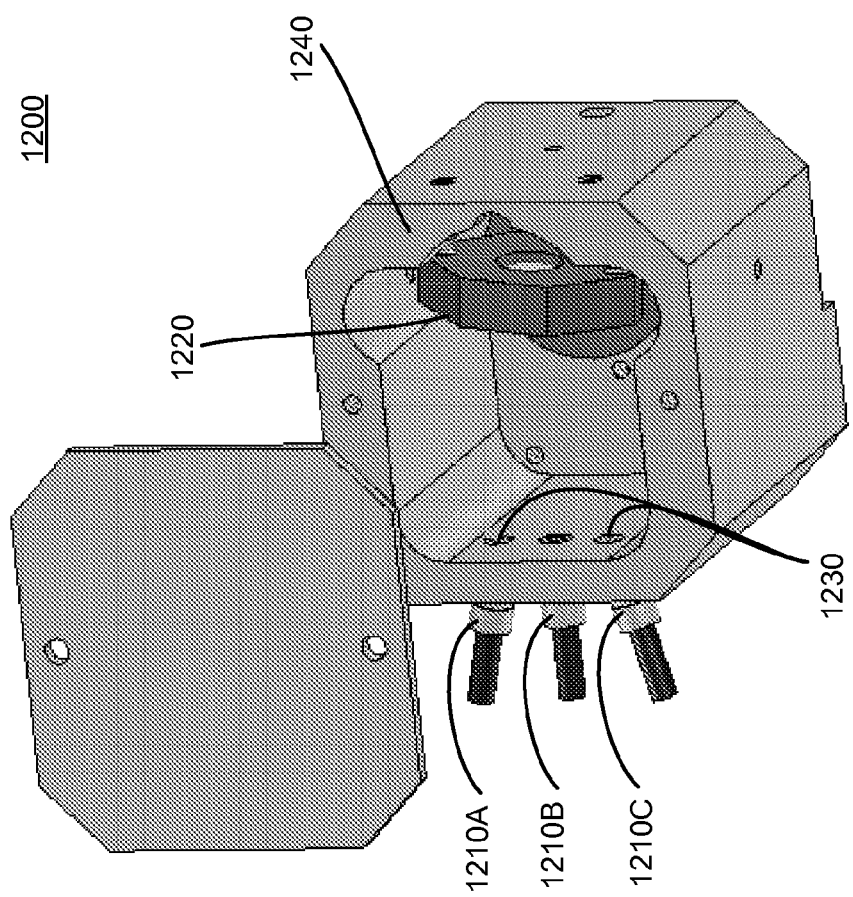
FIG. 12-14 are illustrations of a device for alternating measurements in a spectroscopic measurement system in accordance with one embodiment of the present invention.
Figure 13:
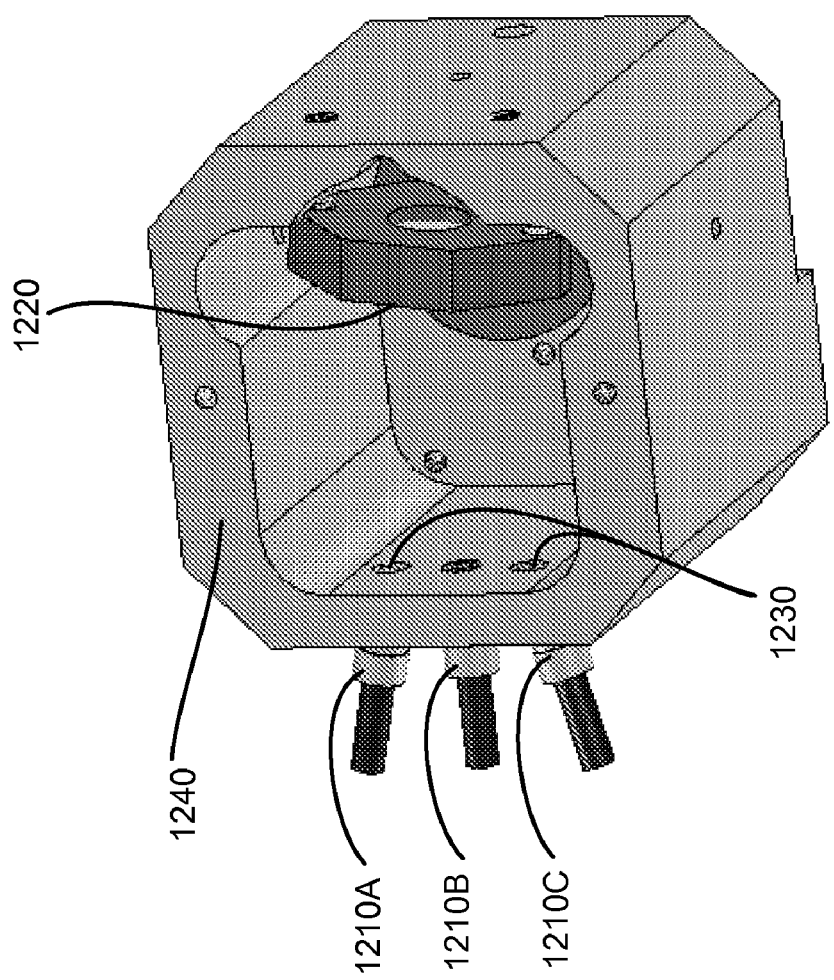
Figure 14:
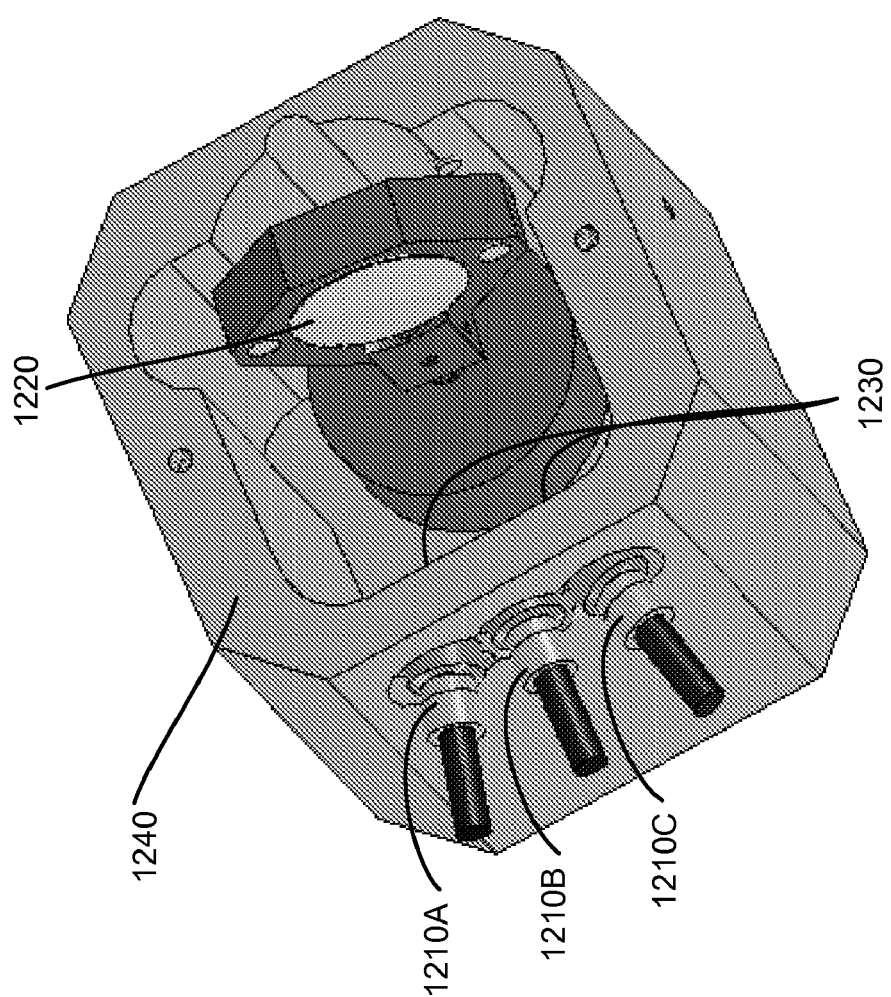
Figure 15:
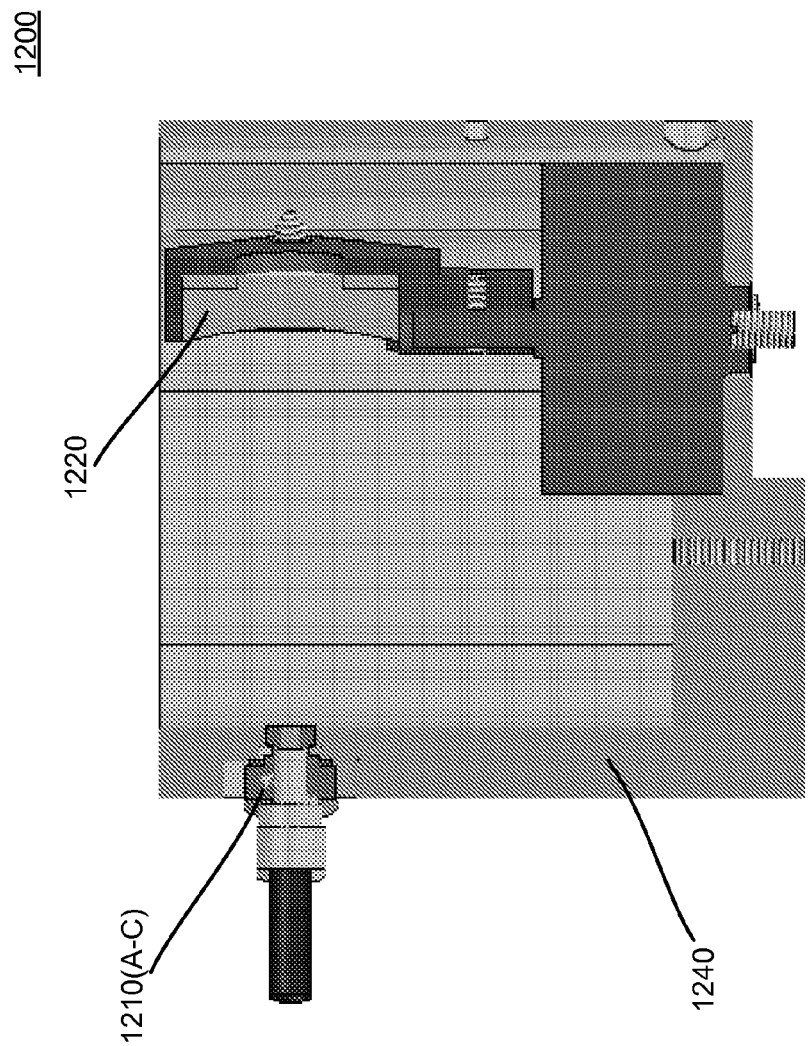
FIG. 15 is a cut-away side view of a device for alternating measurement in a spectroscopic measurement system in accordance with one embodiment of the present invention.

In addition, another embodiment of the present invention includes a device optimized for alternating measurements of the reference and sample in a spectrometer system that utilizes fiber optics. FIGS. 8-11 are illustrations of one implementation of the present invention. Referring first to FIG. 8 the device 800 has a housing 810 with four fiber optic ports 820(A-D). Referring to FIGS. 9-11, for each optic port 820 (A-D) there are optics 830 that convert between the diverging beam entering or exiting a fiber optic 840 connected to the fiber optic port 820(A-D) on the exterior of the housing 810. Internal to the device, the optics 830 convert the illumination to and from a collimated beam 850 when exiting and entering the optic port 820(A-D).

The four ports 820(A-D) are arranged in pairs: each port in a pair 820A-820C, 820B-820D is positioned opposite the other such that illumination exiting one port can be delivered to the other. In the exemplary embodiment shown, the optical axis of the first pair of ports 820A-820C is orthogonal to that of the second pair 820B-820D. Those skilled in the art will be aware of modifications to the arrangement of the ports consistent with the present invention. In many multiplexer designs, either the input or output ports are moved resulting in errors in the measured spectrum associated with lack of mechanical precision. Many embodiments of this device 800 address that limitation by fixing all fiber optic 820(A-D) attachment points. Those skilled in the art will be aware of modifications and variations consistent with the present invention.

Two exemplary modes of operation include: 1) sample illumination provided via fiber optic; and, 2) sample illumination provided by external (non-fiber optic) source. In these exemplary embodiments, the fiber optic ports may be utilized as follows:

(1) Fiber Optic Ports for Fiber Optic Illumination:
Port A 820A: Illumination collected from sample;
Port B 820B: Illumination from source;
Port C 820C: Illumination delivered to spectrometer; and
Port D 820D: Illumination delivered to sample.

The use of a traditional multiplexer in this application would require a fiber optic illuminator with two fiber optic outputs: one to provide illumination directly to the sample and a second attached to the multiplexer to provide a reference source. This design requires only a single attachment to the illumination source.

(2) Fiber Optic Ports for External Illumination:
Port A 820A: Illumination collected from sample;
Port B 820B: Illumination collected from source;
Port C 820C: Illumination delivered to spectrometer; and
Port D 820D: Port not used.

In the second embodiment, the sample is directly illuminated by a source in the measurement head. A fiber optic connected to Port B 820B is used to view this source (either directly or indirectly by viewing a target illuminated by the source).

In addition to the four fiber optic ports 820(A-D) the device 800 has a plate 860 that can be inserted into the illumination beams 850. In the present embodiment, the plate 860 is inserted at a 45-degree angle to all beams 850. FIG. 8 shows the device 800 with this plate 860 in both positions; FIGS. 10 and 11 show the device 800 with the plate 860 in the inserted position; FIG. 9 shows the device 800 with the plate 860 in the removed position. The plate 860 may be made of either a diffuse or specular (mirror) material. Other multiplexer designs utilize moving optics (e.g. mirrors) to redirect illumination from one port to another. Again, there are errors in the measured spectrum associated with lack of mechanical precision. While this device has some of the same problems, the use of a diffuse plate greatly reduces the magnitude of the effect. Also, there are no positional repeatability issues when in "sample mode" as the plate is in the 'removed' position.

In this embodiment, the purpose of the plate 860 is to allow collection of a reference measurement. Reference measurements are acquired with the plate 860 in the inserted position: illumination either directly or indirectly from the source (Port B 820B) is redirected to the port leading to the spectroscopic instrument (Port C 820C). Sample measurements are acquired with the plate 860 in the removed position: the illumination collected from the sample (Port A 820A) is directed to port leading to the spectrometer (Port C 820C). In addition, when the device 800 is in sample measurement mode (plate 860 removed), illumination entering the device 800 from the illumination source (Port B 820B) is directed out Port D 820D—in "fiber optic illumination mode" Port D 820D provides the illumination to the sample; in "external illumination mode" Port D 820D is fitted with a illumination trap as the illumination is not required for sample measurements. Those skilled in the art will be aware of modifications and variations consistent with the present invention.

Now referring to FIGS. 12-15, there are illustrations of another embodiment of the present invention for optimized alternating measurements of the reference and sample in a spectrometer system that utilizes fiber optics. In this embodiment, the device 1200 has three fiber optic ports 1210(A-C). The diverging beam (not shown) associated with each of the three ports 1210(A-C) is aimed at the center point of a concave mirror 1220. In this embodiment, the mirror 1220 is located within a housing 1240 in order to eliminate errors due to external illumination. The focal length of the concave mirror 1220 matches the distance between the mirror 1220 and the ports 1210(A-C). In many multiplexer designs, either the input or output ports are moved resulting in errors in the measured spectrum associated with lack of mechanical precision. This design addresses that limitation as all fiber optic attachment points 1210(A-C) are fixed.

In one embodiment, the fiber optic ports 1210(A-C) may be utilized as follows:
Port A 1210A: Illumination collected from illumination source;
Port B 1210B: Illumination delivered to spectrometer; and
Port C 1210C: Illumination collected from sample.

In this exemplary embodiment, the mirror 1220 is rotated into two positions (hard stops at each end-point). The first position is used for reference measurements and directs illumination collected from the illumination source 1210A to the spectrometer 1210B. The second position is used for sample measurements and directs illumination collected from the sample 1210C to the spectrometer 1210B. In one embodiment, the device contains shutters 1230 that cover the port 1210A, 1210C not being viewed. For example, in the first position, a shutter 1230 would cover the sample port 1210C while illumination from the source 1210A is being redirected by the mirror 1220 to the spectrometer 1210B. Those skilled in the art will realize other means of blocking the unused port, such as a movable guard within the housing 1240, consistent with the present invention. Other multiplexer designs utilize moving optics (e.g. mirrors) to redirect illumination from one port to another. Again, there are errors in the measured spectrum associated with lack of mechanical precision. While this device has some of the same problems, the use of two positions with fixed end-points greatly reduces the magnitude of these effects.

In conclusion, the present invention provides, among other things, a system and method for optical spectroscopic measurements. Those skilled in the art can readily recognize that numerous variations and substitutions may be made in the invention, its use and its configuration to achieve substantially the same results as achieved by the embodiments described herein. Accordingly, there is no intention to limit the invention to the disclosed exemplary forms. Many variations, modifications and alternative constructions fall within the scope and spirit of the disclosed invention as expressed in the claims.

What is claimed is:

1. A measurement head for optical spectroscopic measurements, the measurement head comprising: an illumination source configured to illuminate a sample; a collection optic configured to view the sample; an internal reference, wherein the internal reference is configured to be illuminated by the illumination source and viewed by the collection optic; a calibration mirror, wherein the calibration mirror is configured to allow the internal reference to be viewed by the collection optic.

2. The measurement head of claim 1, wherein the calibration mirror is configured to be moved into a position that would allow the internal reference to be viewed by the collection optic.

3. The measurement head of claim 1, further comprising:
a shutter, wherein the shutter is connected to the internal reference and wherein the shutter is configured to position the internal reference so that the internal reference is illuminated by the illumination source and viewed by the collection optic.

4. The measurement head of claim 1, further comprising:
at least one optical element located between the illumination source and the sample; and
a reflective, illuminator partially surrounding the illumination source, wherein the reflective illuminator is configured to reflect light toward the sample.

5. The measurement head of claim 4, wherein the at least one optical element comprises the collection optic.

6. The measurement head of claim 1, wherein the collection optic is configured to view the sample coaxially with the illumination source.

7. The measurement head of claim 1, wherein the internal reference is configured such that an illumination intensity on the internal reference approximates an illumination intensity on the sample.

8. The measurement head of claim 1, further comprising:
a window disposed between the sample and the illumination source.

9. The measurement head of claim 1, further comprising:
a diffuser radiation shield configured to reduce stray light viewed by the collection optics.

10. The measurement head of claim 1, further comprising:
a UV shield that can be positioned over the internal reference so a to reduce the UV radiation on the internal reference.

11. The measurement head of claim 1, wherein the internal reference is in a fixed position within the measurement head.

12. The measurement head of claim 11, further comprising:
a reflective illuminator partially surrounding the illumination source, wherein the reflective illuminator is configured to reflect light toward the sample; and
wherein the internal reference is positioned between the illumination source and the reflective illuminator.

13. A method for optical spectroscopic measurements, the method comprising: illuminating a sample using an illumination source, wherein the illumination source is located within a measurement head; viewing the sample using a collection optic, wherein the collection optic is located within the measurement head; illuminating an internal reference using the illumination source, wherein the internal reference is located within the measurement head; positioning a calibration mirror such that the collection optic is configured to view the internal reference; and viewing the internal reference using the collection optic.

14. The method of claim 13, further comprising:
moving the internal reference into a position so that it can be viewed by the collection optic.

15. The method of claim 13, farther comprising:
generating light using the illumination source; and
reflecting at east part of the generated light using a reflective illuminator configured to reflect light toward the sample.

16. The method of claim 14, wherein viewing the sample using a collection optic comprises viewing the sample using the collection optic, wherein the collection optic view is co-axially aligned with the illumination source.

17. The method of claim 13, wherein the internal reference is in a fixed position within the measurement head.

18. The method of claim 13, further comprising:
generating light using the illumination source; and
reflecting at least part of the generated light using a reflective illuminator configured to reflect light toward the sample;
wherein the internal reference is in, a fixed position between the illumination source and the sample.

19. A system for optical spectroscopic measurements, the system comprising: a measurement head; an illumination source within the measurement head, wherein the illumination source is configured to illuminate a sample; a collection optic within the measurement head, wherein the collection optic is configured to view the sample; and an internal reference connected to the measurement head, wherein the internal reference is configured to be illuminated by the illumination source and viewed by the collection optic, and wherein the internal reference is in a fixed position within the measurement head.

20. The system of claim 19, further comprising:
a calibration mirror, wherein the calibration mirror can be moved into a position that would avow the internal reference to be viewed by the collection optic.

21. The system of claim 19, further comprising:
a window, wherein the window is disposed between the illumination source and the sample.

22. The system of claim 19, wherein the collection optic is configured to indirectly view the sample.

23. The measurement head of claim 19, further comprising:
a reflective illuminator partially surrounding the illumination source, wherein the reflective illuminator is configured to reflect light toward the sample; and
wherein the internal reference positioned at least partially within a volume created by the reflective illuminator.

* * * * *